(12) United States Patent
Shuros et al.

(10) Patent No.: US 11,285,326 B2
(45) Date of Patent: Mar. 29, 2022

(54) SYSTEMS AND METHODS FOR TREATING CARDIAC ARRHYTHMIAS

(71) Applicant: CARDIAC PACEMAKERS, INC., St. Paul, MN (US)

(72) Inventors: Allan C. Shuros, St. Paul, MN (US); Rodney W. Salo, Fridley, MN (US); Michael J. Kane, Roseville, MN (US); Donald L. Hopper, Maple Grove, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 426 days.

(21) Appl. No.: 15/058,724

(22) Filed: Mar. 2, 2016

(65) Prior Publication Data

US 2016/0256694 A1 Sep. 8, 2016

Related U.S. Application Data

(60) Provisional application No. 62/128,340, filed on Mar. 4, 2015.

(51) Int. Cl.
*A61N 1/365* (2006.01)
*A61B 5/00* (2006.01)
(Continued)

(52) U.S. Cl.
CPC ........ *A61N 1/36585* (2013.01); *A61B 5/0816* (2013.01); *A61B 5/4836* (2013.01);
(Continued)

(58) Field of Classification Search
CPC ............... A61N 1/36585; A61N 1/3756; A61N 1/3621; A61N 1/36592; A61N 1/36514;
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

AU 2008279789 B2 10/2011
AU 2008329620 B2 5/2014
(Continued)

OTHER PUBLICATIONS

US 8,886,318 B2, 11/2014, Jacobson et al. (withdrawn)
(Continued)

*Primary Examiner* — Mallika D Fairchild
*Assistant Examiner* — Minh Duc G Pham
(74) *Attorney, Agent, or Firm* — Seager, Tufte & Wickhem LLP.

(57) ABSTRACT

Systems and methods for rate-adaptive pacing are disclosed. In one illustrative embodiment, a medical device for delivering electrical stimulation to a heart may include a housing configured to be implanted on the heart or within a chamber of the heart, one or more electrodes connected to the housing, and a controller disposed within the housing. The controller may be configured to sense a first signal and determine a respiration rate based at least in part on the sensed first signal. In at least some embodiments, the controller may be further configured to adjust a rate of delivery of electrical stimulation by the medical device based at least in part on the determined respiration rate.

14 Claims, 7 Drawing Sheets

(51) Int. Cl.
- *A61B 5/08* (2006.01)
- *A61N 1/375* (2006.01)
- *A61B 5/091* (2006.01)
- *A61B 5/113* (2006.01)
- *A61N 1/372* (2006.01)
- *A61N 1/05* (2006.01)
- *A61B 5/0538* (2021.01)

(52) U.S. Cl.
CPC ............ *A61B 5/686* (2013.01); *A61B 5/6869* (2013.01); *A61N 1/36514* (2013.01); *A61N 1/36542* (2013.01); *A61N 1/3756* (2013.01); *A61B 5/0538* (2013.01); *A61B 5/091* (2013.01); *A61B 5/113* (2013.01); *A61B 2562/0219* (2013.01); *A61B 2562/0247* (2013.01); *A61N 1/0587* (2013.01); *A61N 1/36578* (2013.01); *A61N 1/37205* (2013.01)

(58) Field of Classification Search
CPC .............. A61N 1/36542; A61N 1/3706; A61N 1/37205; A61B 5/02405; A61B 5/7275; A61B 5/0816; A61B 5/6869
USPC .......................................................... 607/18
See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,630,614 A * | 12/1986 | Atlas .................... A61B 5/0816 600/534 |
| 4,635,639 A | 1/1987 | Akala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,197 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |

(56) References Cited

U.S. PATENT DOCUMENTS

| | | |
|---|---|---|
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,974,340 A | 10/1999 | Kadhiresan |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |

(56) References Cited

U.S. PATENT DOCUMENTS

| | | |
|---|---|---|
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |

(56) References Cited

U.S. PATENT DOCUMENTS

| | | |
|---|---|---|
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Phanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |

(56) References Cited

U.S. PATENT DOCUMENTS

| | | |
|---|---|---|
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |

(56) References Cited

U.S. PATENT DOCUMENTS

| | | |
|---|---|---|
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Nojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0161657 A1 | 7/2008 | Bullens et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Nillis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030085 A1 | 2/2010 | Rojas Ojeda et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0298732 A1 | 11/2010 | Zhang et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Gowan et al. |
| 2011/0166621 A1 | 7/2011 | Gowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |

(56) References Cited

U.S. PATENT DOCUMENTS

| | | |
|---|---|---|
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | D'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197323 A1 | 8/2012 | Elferri et al. |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Ran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172034 A1 | 6/2014 | Bornzin et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228692 A1* | 8/2014 | Chan .............. A61B 5/4818 600/484 |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |

(56) References Cited

U.S. PATENT DOCUMENTS

| | | |
|---|---|---|
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1* | 6/2015 | Demmer ............. A61B 5/1118 600/595 |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |

FOREIGN PATENT DOCUMENTS

| | | |
|---|---|---|
| AU | 2014203793 A1 | 7/2014 |
| CA | 1003904 A1 | 1/1977 |
| CN | 102753095 A | 10/2012 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2011098944 A1 | 8/2011 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

Notification of Transmittal of the International Search Report and the Written Opinion of the International Searching Authority, or the Declaration for Application No. PCT/US2016/020432, 15 pages, dated Jul. 22, 2016.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Seyedi et al., "A Survey on Intrabody Communications for Body Area Network Application," IEEE Transactions on Biomedical Engineering,vol. 60(8): 2067-2079, 2013.

Wegmüller, "Intra-Body Communication for Biomedical Sensor Networks," Diss. ETH, No. 17323, 1-173, 2007.

Notification of Transmittal of the International Search Report and the Written Opinion of the International Searching Authority, or the Declaration, dated Jan. 29, 2016, 15 pages.

Spickler et al., "Totally Self Contained Intracardiac Pacemaker," Journal of Electrocardiology, vol. 3(3&4): 324-331, 1970.

"Instructions for Use System 1, Leadless Cardiac Pacemaker (LCP) and Delivery Catheter," Nanostim Leadless Pacemakers, pp. 1-28, 2013.

* cited by examiner

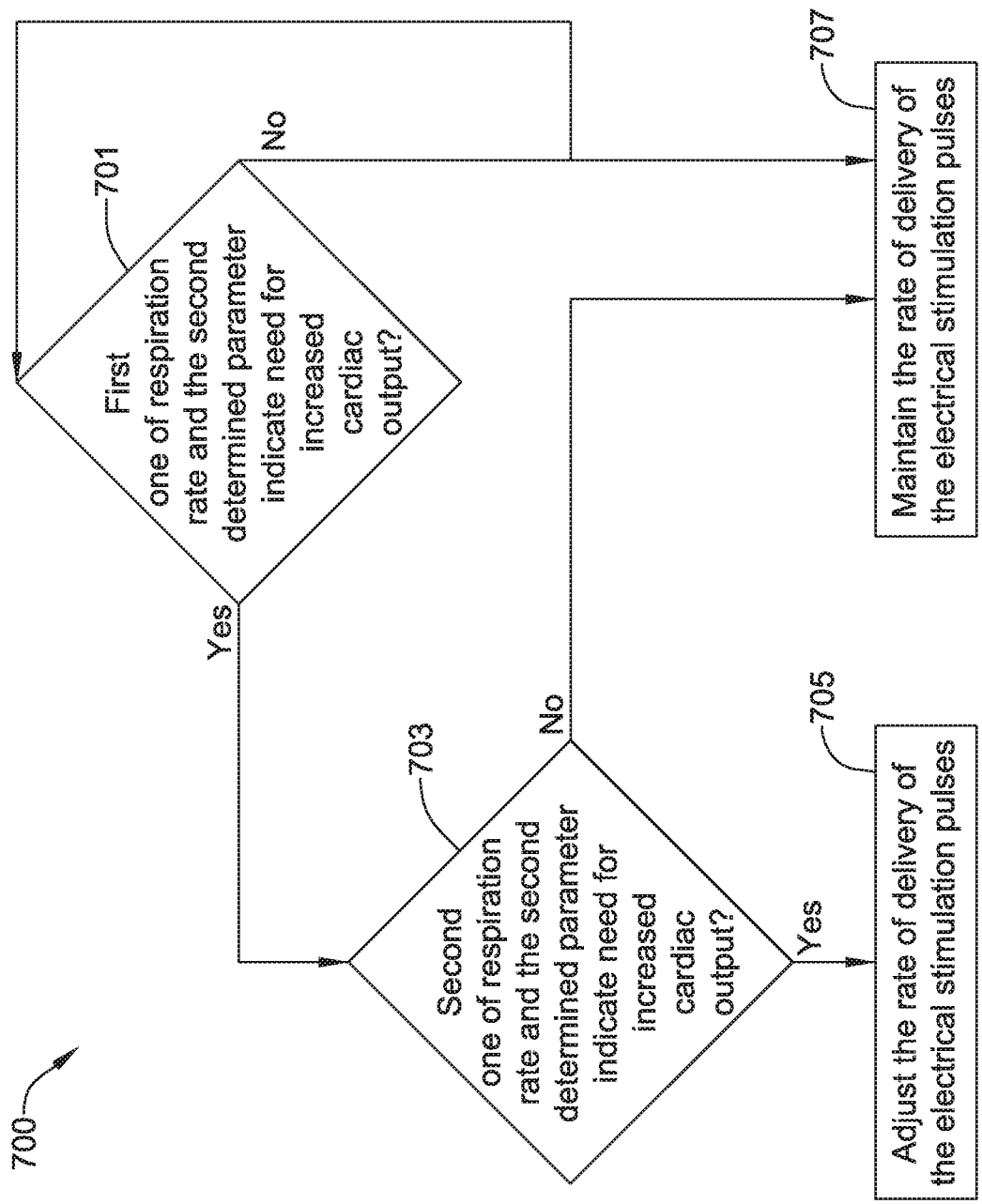

SYSTEMS AND METHODS FOR TREATING CARDIAC ARRHYTHMIAS

CROSS REFERENCE TO RELATED APPLICATIONS

This application claims the benefit of U.S. Provisional Patent Application Ser. No. 62/128,340 filed on Mar. 4, 2015, the disclosures of each incorporated herein by reference.

TECHNICAL FIELD

The present disclosure generally relates to systems, devices, and methods for treating cardiac arrhythmias, and more particularly, to systems, devices, and methods for implementing rate adaptive pacing.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) have been implanted in a patient's body. Such devices may monitor and provide electrical stimulation to the heart to help the heart operate in a more normal, efficient and/or safe manner. In some cases, a patient may have multiple implanted devices.

SUMMARY

The present disclosure generally relates to systems, devices, and methods for treating cardiac arrhythmias, and more particularly, to systems, devices, and methods for implementing rate adaptive pacing. In one illustrative embodiment, a medical device for delivering electrical stimulation to a heart may comprise a housing configured to be implanted on the heart or within a chamber of the heart, one or more electrodes connected to the housing, and a controller disposed within the housing. The controller may be configured to sense a first signal and determine a respiration rate based at least in part on the sensed first signal. In at least some embodiments, the controller may be configured to adjust a rate of delivery of electrical stimulation by the medical device based at least in part on the determined respiration rate.

In some instances, the controller may include one or more sensors, such as one or more accelerometers, impedance sensors, pressure sensors, piezoelectric sensors and/or the like. In some cases, the controller may include a sense amplifier or the like connected to one or more of the electrodes of the medical device for directly sensing a signal via the one or more electrodes of the medical device.

Additionally or alternatively, in the above illustrative embodiment, the controller may be further configured to determine a relative tidal volume parameter based at least in part on the sensed first signal, and adjust the rate of delivery of electrical stimulation by the medical device based at least in part on both the determined respiration rate and the determined relative tidal volume parameter.

Additionally, or alternatively, in any of the above illustrative embodiments, the sensed first signal is an accelerometer signal.

Additionally, or alternatively, in any of the above illustrative embodiments, the sensed first signal is a temperature signal.

Additionally, or alternatively, in any of the above illustrative embodiments, the sensed first signal is pressure signal.

Additionally, or alternatively, in any of the above illustrative embodiments, the sensed first signal is a strain signal.

Additionally, or alternatively, in any of the above illustrative embodiments, the sensed first signal is an electrocardiogram (ECG).

Additionally, or alternatively, in any of the above illustrative embodiments, the controller is configured to adjust the rate of delivery of electrical stimulation by the medical device if the determined respiration rate rises above a respiration threshold.

Additionally, or alternatively, in any of the above illustrative embodiments, the controller is configured to adjust the rate of delivery of electrical stimulation by the medical device if the determined respiration rate falls equal to or below a respiration threshold.

Additionally, or alternatively, in any of the above illustrative embodiments, the controller is further configured to sense a second signal, and adjust the rate of delivery of electrical stimulation by the medical device based at least in part on the determined respiration rate and the second sensed signal.

Additionally, or alternatively, in any of the above illustrative embodiments, the second sensed signal is a heart sounds signal.

Additionally, or alternatively, in any of the above illustrative embodiments, the controller is configured to increase the rate of delivery of electrical stimulation by the medical device if the respiration rate rises above a respiration threshold and the second sensed signal rises above a second threshold.

Additionally, or alternatively, in any of the above illustrative embodiments, to determine a respiration rate based at least in part on the sensed first signal, the controller is configured to determine an absolute value of the sensed first signal.

Additionally, or alternatively, in any of the above illustrative embodiments, to determine a respiration rate based at least in part on the sensed first signal, the controller is further configured to determine an integral of the absolute value of the sensed first signal.

Additionally, or alternatively, in any of the above illustrative embodiments, to determine a respiration rate based at least in part on the sensed first signal, the controller is further configured to filter the integrated signal with a low-pass filter.

Additionally, or alternatively, in any of the above illustrative embodiments, the low pass filter has a corner frequency of between 0.3 Hz and 0.7 Hz.

Additionally, or alternatively, in any of the above illustrative embodiments, to determine a respiration rate based at least in part on the sensed first signal, the controller is further configured to determine the zero crossings of the first derivative of the low-pass filtered signal.

Additionally, or alternatively, in any of the above illustrative embodiments, to determine a respiration rate based at least in part on the sensed first signal, the controller is further configured to determine a difference in timing between a pair of zero crossings of the first derivative of the low-pass filtered signal.

Additionally, or alternatively, in any of the above illustrative embodiments, the controller may further be configured to sample the first signal at fixed points of the cardiac cycle of the heart.

Additionally, or alternatively, in any of the above illustrative embodiments, the controller may further be configured to sample the first signal at occurrences of R-waves in a sensed electrocardiogram (ECG).

Additionally, or alternatively, in any of the above illustrative embodiments, to determine a respiration rate based at least in part on the sensed first signal, the controller may be further configured to filter the first sensed signal with a low pass filter.

In another illustrative embodiment, a method of delivering electrical stimulation to a heart may comprise delivering electrical stimulation to the heart at a first rate of delivery with a leadless cardiac pacemaker (LCP) configured to be implanted on the heart or within a chamber of the heart. The method may include sensing a first signal with the LCP and determining whether to change the rate of delivery of the electrical stimulation based at least in part on the first sensed signal. In at least some illustrative embodiments, the method may additionally include, after determining to change the rate of delivery of the electrical stimulation, delivering electrical stimulation to the heart at a second rate of delivery with the LCP.

Additionally, or alternatively, in the above illustrative embodiment, the method may further include determining a respiration rate based on the first sensed signal.

Additionally, or alternatively, in any of the above illustrative embodiments, the first sensed signal is an accelerometer signal.

Additionally, or alternatively, in any of the above illustrative embodiments, the second rate of delivery is determined based at least in part on a gain factor.

In still another illustrative embodiments, a medical device for delivering electrical stimulation to a heart may comprise a housing configured to be implanted on the heart or within a chamber of the heart, one or more electrodes connected to the housing, and a controller disposed within the housing. In some illustrative embodiments, the controller may be configured to sense a first signal and determine a respiration rate based at least in part on the sensed first signal. In at least some illustrative embodiments, the controller may further be configured to adjust a rate of delivery of electrical stimulation by the medical device based at least in part on the determined respiration rate.

In some instances, the controller may include one or more sensors, such as one or more accelerometers, impedance sensors, pressure sensors, piezoelectric sensors and/or the like. In some cases, the controller may include a sense amplifier or the like connected to one or more of the electrodes of the medical device for directly sensing a signal via the one or more electrodes of the medical device.

Additionally, or alternatively, in the above illustrative embodiment, the controller may be further configured to determine a relative tidal volume parameter based at least in part on the sensed first signal, and adjust the rate of delivery of electrical stimulation by the medical device based at least in part on both the determined respiration rate and the determined relative tidal volume parameter.

Additionally, or alternatively, in any of the above illustrative embodiments, the sensed first signal is an acceleration signal.

Additionally, or alternatively, in any of the above illustrative embodiments, the sensed first signal is an electrocardiogram (ECG).

Additionally, or alternatively, in any of the above illustrative embodiments, the controller is configured to adjust the rate of delivery of electrical stimulation by the medical device if the determined respiration rate rises above a respiration threshold.

Additionally, or alternatively, in any of the above illustrative embodiments, the controller is configured to adjust the rate of delivery of electrical stimulation by the medical device if the determined respiration rate falls equal to or below a respiration threshold.

Additionally, or alternatively, in any of the above illustrative embodiments, the controller is further configured to sense a second signal, and adjust the rate of delivery of electrical stimulation by the medical device based at least in part on the determined respiration rate and the second sensed signal.

Additionally, or alternatively, in any of the above illustrative embodiments, the second sensed signal is a heart sounds signal.

Additionally, or alternatively, in any of the above illustrative embodiments, the controller is configured to increase the rate of delivery of electrical stimulation by the medical device if the respiration rate rises above a respiration threshold and the second sensed signal rises above a second threshold.

Additionally, or alternatively, in any of the above illustrative embodiments, the medical device is a leadless cardiac pacemaker.

In another illustrative embodiment, a method of delivering electrical stimulation to a heart may comprise sensing a first signal with a leadless cardiac pacemaker (LCP) configured to be implanted on the heart or within a chamber of the heart and determining an absolute value of the first sensed signal. The method may include determining an integrated signal based on the absolute value of the first sensed signal and determining a respiration rate based at least in part on the integrated signal. In at least some illustrative embodiments, the method may further include changing a rate of delivery of electrical stimulation based at least in part on changes in the respiration rate.

Additionally, or alternatively, in the above illustrative embodiment, determining a respiration rate based on the integrated signal comprises determining a difference in timing between a pair of peaks of the integrated signal.

Additionally, or alternatively, in any of the above illustrative embodiments, the value each peak of the pair of peaks are local maximums.

Additionally, or alternatively, in any of the above illustrative embodiments, determining a respiration rate based on the integrated signal further comprises low-pass filtering the integrated signal, determining zero-crossings of the first derivative of the low-pass filtered signal, and determining a difference in timing between a pair of zero-crossings of the first derivative of the low-pass filtered signal.

Additionally, or alternatively, in any of the above illustrative embodiments, the first sensed signal is an accelerometer signal.

Additionally, or alternatively, in any of the above illustrative embodiments, the first sensed signal is an electrocardiogram (ECG).

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which:

FIG. 7 is a flow diagram of an illustrative method that may be implemented by a medical device or medical device system, such as the illustrative LCP of FIG. 1.

Figure 1:
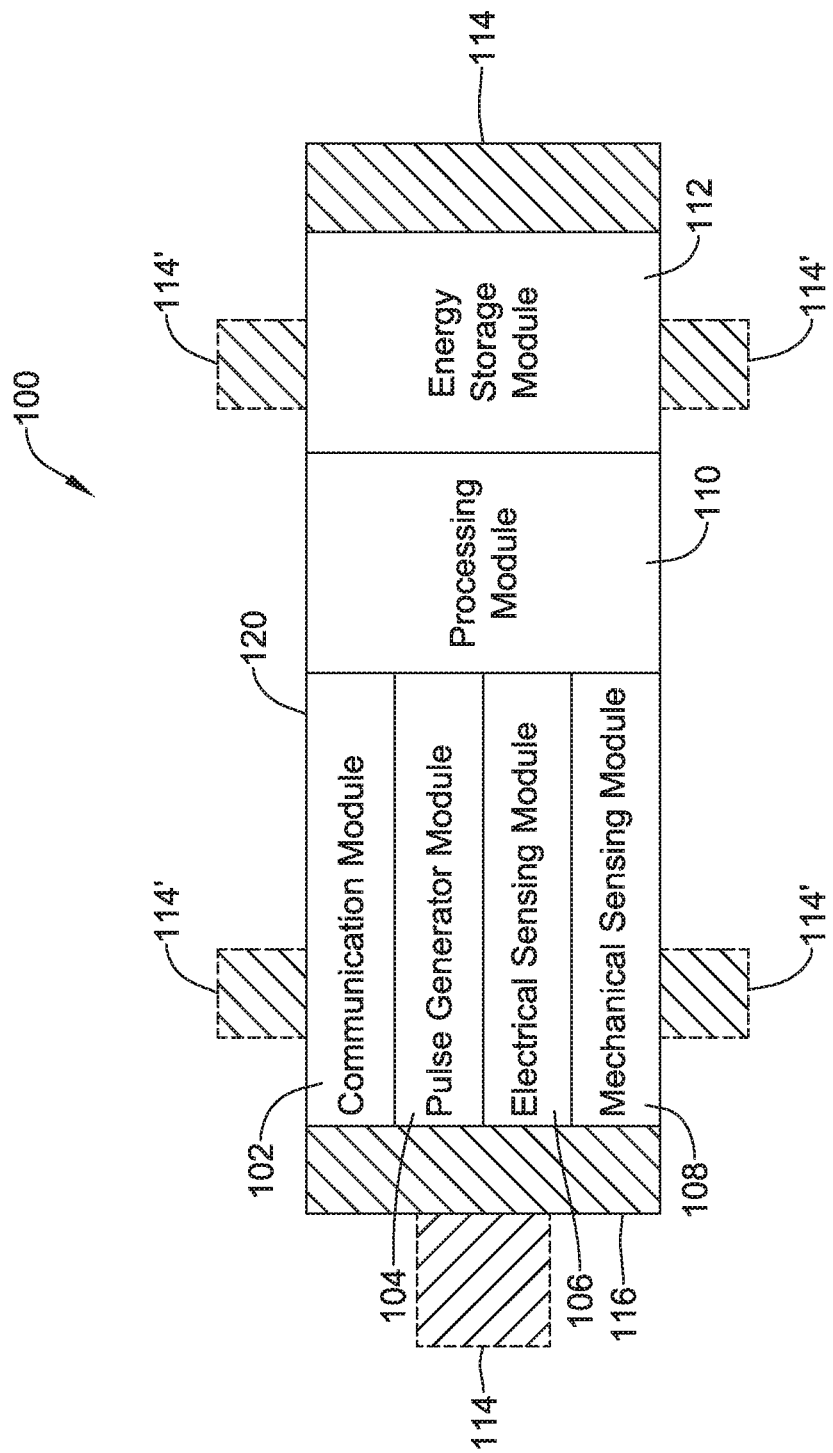
FIG. 1 is a schematic block diagram of an illustrative leadless cardiac pacemaker (LCP) according to one illustrative embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

This disclosure describes systems, devices, and methods for delivering electrical stimulation to a heart in a rate adaptive manner. Healthy people's bodies generally adjust the rate at which their hearts beat in response to higher or lower metabolic needs, for example during exercise or in response to various external stimuli. However, some people develop diseases or conditions which affect their bodies' abilities to cause their hearts to contract in an effective manner. Accordingly, devices in accordance with the present disclosure may be implanted in such people. In some instances, the implanted devices may deliver electrical stimulation on an on-going basis and adjust the rate of delivered electrical stimulation in accordance with sensed physiological parameters indicative of increased metabolic needs.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator 104 generates the electrical stimulation pulses, for example in rate adaptive pacing. In another embodiment, the electrical stimulation pulses may be defibrillation/cardioversion pulses for shocking the heart out of fibrillation or into a normal heart rhythm. In yet another embodiment, the electrical stimulation pulses may be anti-tachycardia pacing (ATP) pulses. These are just some examples. When used to treat other ailments, the pulse generator module 104 may generate electrical stimulation pulses suitable for neuro-stimulation therapy or the like. Pulse generator module 104 may include one or more capacitor elements and/or other charge storage devices to aid in generating and delivering appropriate electrical stimulation pulses. In the embodiment shown, pulse generator module 104 may use energy stored in energy storage module 112 to generate the electrical stimulation pulses. In some examples, pulse generator module 104 may include a switching circuit that is connected to energy storage module 112 and may connect energy storage module 112 to one or more of electrodes 114/114' to generate electrical stimulation pulses.

Pulse generator module 104 may include the capability to modify the electrical stimulation pulses, such as by adjusting the pulse width and/or amplitude of the electrical stimulation pulses. When pacing the heart, this may help tailor the electrical stimulation pulses to capture the heart a particular patient, sometimes with reduced battery usage. For neuro-stimulation therapy, adjusting the pulse width and/or amplitude may help tailor the therapy for a particular application and/or help make the therapy more effective for a particular patient.

Although depicted as separate modules, in some embodiments, LCP 100 may include a combined communication module 102/pulse generator module 104. For instance, pulse generator module 104 may be configured to also generate electrical communication signals. In such embodiments, pulse generator 104 may be configured to generate and deliver both electrical communication signals and electrical stimulation pulses.

In some embodiments, LCP 100 may include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias. Processing module 110 may further receive information from communication module 102. In some embodiments, processing module 110 may additionally use such received information to determine occurrences and types of arrhythmias. However, in other embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator 104 generates electrical stimulation pulses.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

In some instances, LCP 100 may be configured to deliver rate-adaptive pacing therapy to a patient's heart. For instance, LCP 100 may be configured to deliver electrical stimulation pulses to the heart of the patient on an on-going basis to help ensure that the patient's heart contracts in a safe and effective manner. LCP 100 may additionally sense one or more signals, for example using electrical sensing module 106 and/or mechanical sensing module 108, and determine, based on the sensed one or more signals, whether to change the rate of delivery of the electrical stimulation pulses. For example, based on the sensed one or more signals, LCP 100 may determine that there is less of a need for cardiac output, and may decrease the rate of delivery of the electrical stimulation pulses. In other instances, based on the one or more sensed signals, LCP 100 may determine that there is a need for increased cardiac output, and may increase the rate of delivery of the electrical stimulation pulses. Adjusting the rate of delivery of the electrical stimulation pulses based on the sensed one or more signals may extend the battery life of LCP 100 by only requiring higher rates of delivery of electrical stimulation pulses when the sensed one or more signals indicate there is a need for increased cardiac output. Additionally, adjusting the rate of delivery of the electrical stimulation pulses may increase a comfort level of the patient by more closely matching the rate of delivery of electrical stimulation pulses with the cardiac output need of the patient.

Where LCP 100 adjusts the rate of delivery of electrical stimulation pulses based on the sensed one or more signals, LCP 100 may in some cases determine a respiration rate based on the sensed one or more signals. Respiration rate may be indicative of a relative cardiac output need for the patient. For example, an increased respiration rate may indicate that there is a need for increased cardiac output, and a decreased respiration rate may indicate less of a need for cardiac output. Accordingly, and when so provided, LCP 100 may adjust the rate of delivery of the electrical stimulation pulses based on the determined respiration rate.

In at least some examples, LCP 100 may include an accelerometer and may determine a measure related to the respiration rate based on the sensed accelerometer signal. Where LCP 100 is implanted on a patient's heart or within the heart, the accelerometer signal may include signals indicative of movement related to a number of different causes. For instance, the accelerometer signal may include movement related to the gross movement of the patient, such as walking, bending, or other gross body movements. Additionally, the accelerometer signal may include movement related to the contraction of the heart, particularly when LCP 100 is implanted on or within the heart. Additionally, the accelerometer signal may include movement related to the inhalation and exhalation of the patient (i.e. respiration). For instance, as a patient breathes in and out, the lungs apply different pressure to the heart and the intrathoracic pressure changes accordingly. This change in the intrathoracic pressure may cause changes in the shape and size of the various chambers of the heart, as well as the movement of the heart and the heart chambers. After inhalation, the intrathoracic pressure may be relatively higher, which may decrease the volume of blood that flows into one or more of the chambers of the heart during a cardiac cycle. Conversely, after exhalation, the intrathoracic pressure may be relatively lower, which may allow relatively more blood to enter the chambers of the heart during a cardiac cycle. These differences in the amount of blood flowing into and out of the heart and any movement of the heart or heart chambers due to the changes in intrathoracic pressure may be contained in the accelerometer signal.

Figure 2:
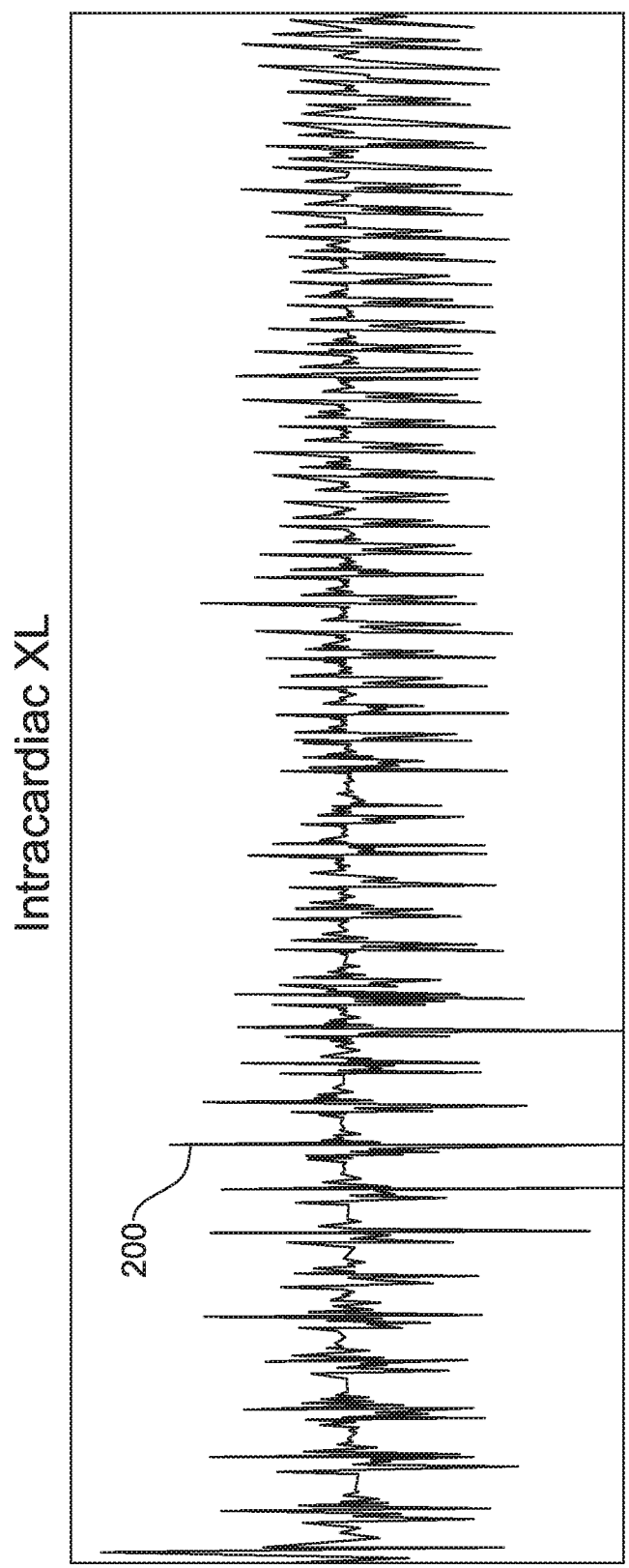
FIG. 2 is a graph of illustrative raw accelerometer data plotted over a number of cardiac cycles.
Figure 3:
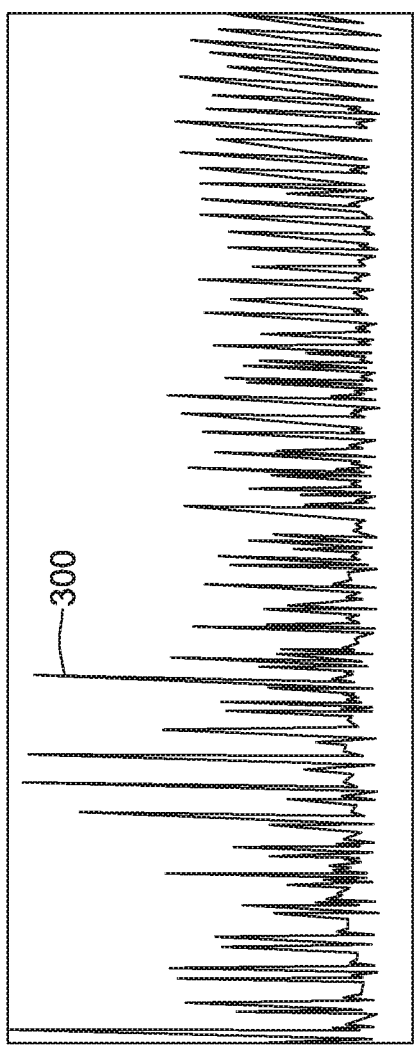
FIG. 3 is a graph of the absolute value of the illustrative raw accelerometer data of FIG. 2.
Figure 4:
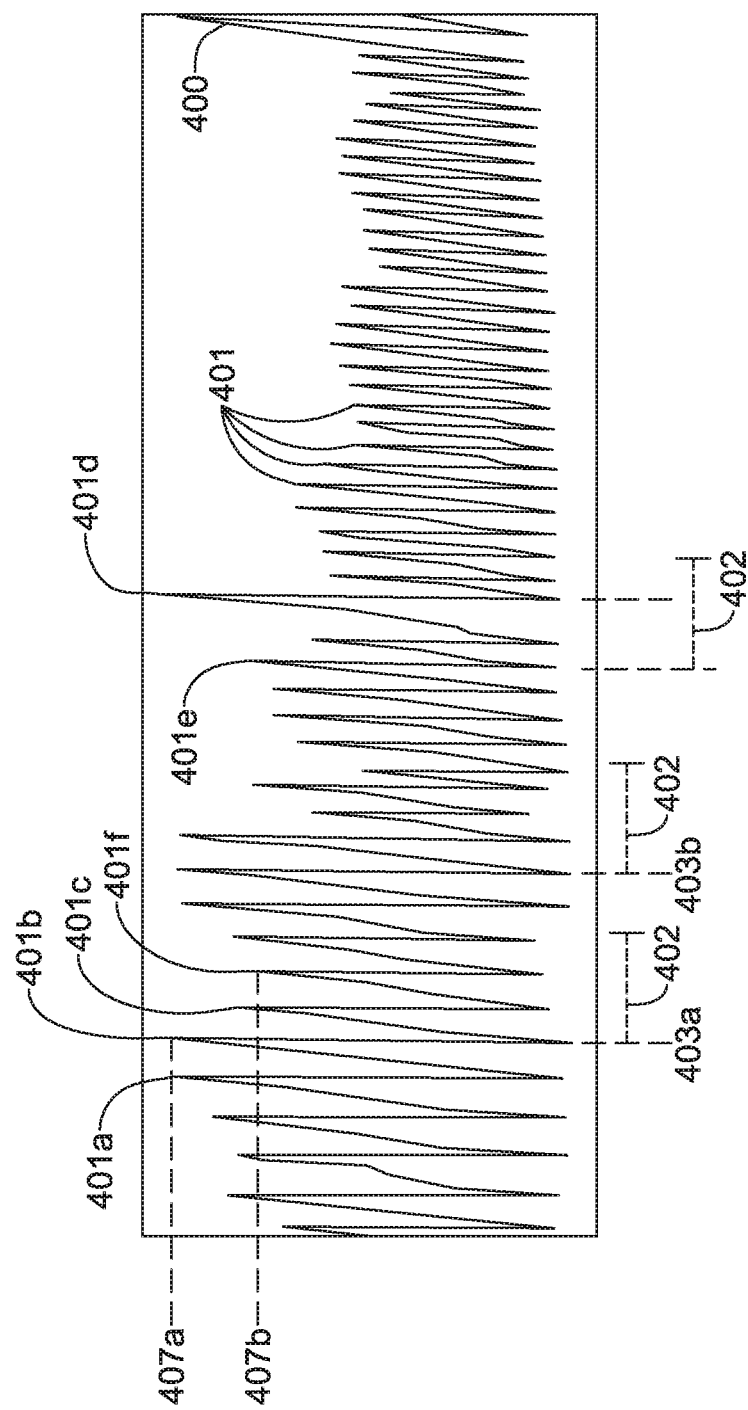
FIG. 4 is a graph of an integrated signal based on the absolute value of the illustrative raw accelerometer data of FIG. 3.

FIGS. 2-4 depict example accelerometer data and processed accelerometer data that may facilitate LCP 100 in determining a respiration rate. FIG. 2 depicts raw accelerometer data 200 taken over a period of time. In this instance, raw accelerometer data 200 represents accelerometer data captured over a number of cardiac cycles. Raw accelerometer data 200 may represent a signal output from an accelerometer of LCP 100 when LCP 100 is implanted within a patient's heart chamber.

To help determine a respiration rate, LCP 100 may process the raw accelerometer data 200 in any suitable manner. In at least some examples, LCP 100 may begin by determining an absolute value of raw accelerometer data 200, as shown in FIG. 3 and represented by absolute value data 300. Thereafter, LCP 100 may determine an integrated signal 400, or integral, of the absolute value data 300. In some instances, LCP 100 may determine the integrated signal 400 of absolute value data 300 over each cardiac cycle. LCP 100 may identify each cardiac cycle based on, for example, the positioning of R-wave peaks. Integrated signal 400 depicts what such an integrated signal of absolute value data 300 may look like.

After determining integrated signal 400, LCP 100 may determine one or more respiration rates directly from integrated signal 400. As one example, LCP 100 may determine exhalation times, identified as exhalation times 403a-b. To find the exhalation times, LCP 100 may determine which of peaks 401 of integrated signal 400 represent local maximums. For instance, LCP 100 may determine that peak 401b has a greater maximum value than either of peaks 401a or 401c, which occur just prior to 401b and just subsequent to peak 401b respectively. Accordingly, LCP 100 may determine that the beginning of exhalation time 403a is in alignment with peak 401b. Using a similar methodology, LCP 100 may determine the beginning of another exhalation time at 403b. LCP 100 may divide sixty seconds by the difference in time between two successive exhalation times, such as exhalation times 403a and 403b, to determine a respiration rate. For instance, if exhalation times 403a and 403b are two seconds apart, LCP 100 may determine the respiration rate to be 30 breaths per minute. Of course, in other examples, LCP 100 may determine a respiration rate based on identified local minimums. LCP 100 may determine times of local minimums in a similar manner to how LCP 100 may determine local maximums, except LCP 100 may identify peaks that have lower values than other nearby peaks.

In some instances, LCP 100 may employ one or more enhancements to the method described above. For instance, LCP 100 may only determine one of peaks 401 that correspond to a local maximum corresponds to the beginning of an exhalation time if the identified peak 401 is not within a threshold time of the previous peak determined to be a local maximum. For instance, looking at integrated signal 400, although peak 401d is a local maximum, peak 401d occurs within blanking period 402 of local maximum peak 401e. Accordingly, LCP 100 may not consider peak 401d as corresponding to the beginning of an exhalation time. LCP 100 may reset blanking period 402 after each determination of the beginning of an exhalation time. Blanking period 402 may help smooth out the determined respiration and help ensure that the respiration rate is not significantly affected by artifacts that affect the accelerometer signal from sources other than inhalation and exhalation. In some cases, blanking period 402 may range anywhere from one-quarter of a second to one second or more. In some instances, LCP 100 402 may adjust blanking period 402 based on the last known good respiration rate or an expected respiration rate. Additionally, in some instances, LCP 100 402 may adjust blanking period 402, for example based on one or more other sensed signals. The blanking period 402 may be adjusted down as the respiration rate increases, and visa-versa.

Another example of an enhancement includes not determining local maximums as corresponding to a beginning of an exhalation time if the identified local maximums have maximum values outside of a maximum value range. For instance, if a local maximum has a value that is greater than the maximum value range, LCP 100 may not determine the local maximum as corresponding to a beginning of an exhalation time. In some instances, the maximum value range may be an average of the values of the previous three, five, ten, or any other suitable number of peaks. In other instances, the maximum value range may be the mean of the maximum peak values over the last minute. In some additional instances, the maximum value range may be the mean of the maximum peak values over the last minute plus or minus a standard deviation. Alternatively, instead of the maximum value range corresponding to the maximum value of the peaks, the maximum value range could correspond to an amplitude, with the amplitude being measured by the distance between the identified peak and the previous, or subsequent, valley.

In some examples, LCP 100 may determine an overall respiration rate that is a rolling average of five respiration rates determined by the difference in timings of five successive pairs of exhalation times. However, the exact number of respiration rates used to determine the overall respiration rate may differ in other examples. In alternative cases, the overall respiration rate may be the most recent determined respiration rate. These are just some examples of how LCP 100 may determine an overall respiration rate based on integrated signal 400.

Once LCP 100 has determined an overall respiration rate, LCP 100 may determine whether to adjust the rate at which LCP 100 is delivering electrical stimulation pulses. In some instances, LCP 100 may use thresholding to determine an appropriate rate of electrical stimulation delivery. As one example, LCP 100 may have a number of respiration rate thresholds stored in memory, and each respiration rate threshold may be associated with a different rate of electrical stimulation delivery. As the respiration rate rises above each respiration rate threshold, or falls equal to or below each respiration rate threshold, LCP 100 may adjust the rate of delivery of electrical stimulation pulses based on the rate associated with the appropriate threshold. As one example, LCP 100 may have respiration rate thresholds of ten breathes per minute, twenty breaths per minute, and thirty breaths per minute, and the respiration rate threshold of twenty breaths per minute is associated with a rate of delivery of electrical stimulation of seventy stimulation pulses per minute (e.g. 70 beats/minute). In such an example, while the overall respiration rate is greater than twenty breaths per minute and less than or equal to thirty breaths per minute, LCP 100 may deliver electrical stimulation pulses at a rate of seventy pulses per minute. Once LCP 100 determines that the overall respiration rate has risen above the thirty breaths per minute respiration rate threshold, LCP 100 may increase the rate of delivery of electrical stimulation pulses to the rate associated with the thirty breaths per minute respiration rate threshold, for example ninety beats per minute (e.g. 90 beats/minute). In this manner, LCP 100 may adjust the rate of delivery of electrical stimulation pulses based on the overall respiration rate.

In some alternative embodiments, LCP 100 may adjust the rate of delivery of electrical stimulation pulses based on a gain factor related to the overall respiration rate. For instance, the gain factor may be a factor multiplied by the percentage change in the respiration rate from a baseline respiration rate. As one example, the baseline respiration rate may be ten breathes per minute. While the overall respiration rate is ten breathes per minute, LCP 100 may deliver electrical stimulation pulses, for example, at a rate of sixty pulses per minute (e.g. 60 beats/minute). If the overall respiration rate rises to twenty breathes per minute, the change in the overall respiration rate is one-hundred percent. If the gain factor is set to 0.5, LCP 100 may then increase the rate of delivery of electrical stimulation pulses by 50%, to ninety pulses per minute (e.g. 90 beats/minute). It should be understood that a gain factor of 0.5 is only used as an example. The gain factor may be any suitable number, which may vary between patients. In other instances, the gain factor may be related to the relative change in the overall respiration rate, for instance between the most recent overall respiration rate and a newly determined and different overall respiration rate. In at least some embodiments, LCP 100 may have a minimum threshold of change in the overall respiration rate that must be reached before LCP 100 adjusts the rate of electrical stimulation delivery.

Regardless of the specific method that LCP 100 employs to adjust the rate of delivery of electrical stimulation pulses, LCP 100 may have programmed maximum and minimum rates. For instance, even if the method used to adjust the rate of delivery of the electrical stimulation pulses would cause LCP 100 to adjust the rate of delivery of the electrical stimulation pulses above the maximum threshold, LCP 100 may only deliver the electrical stimulation pulses at the maximum rate. Additionally, even if the method used to adjust the rate of delivery of electrical stimulation pulses would cause LCP 100 to adjust the rate of delivery of the electrical stimulation pulses below the minimum threshold, LCP 100 may only deliver the electrical stimulation pulses at the minimum rate.

Figure 5:
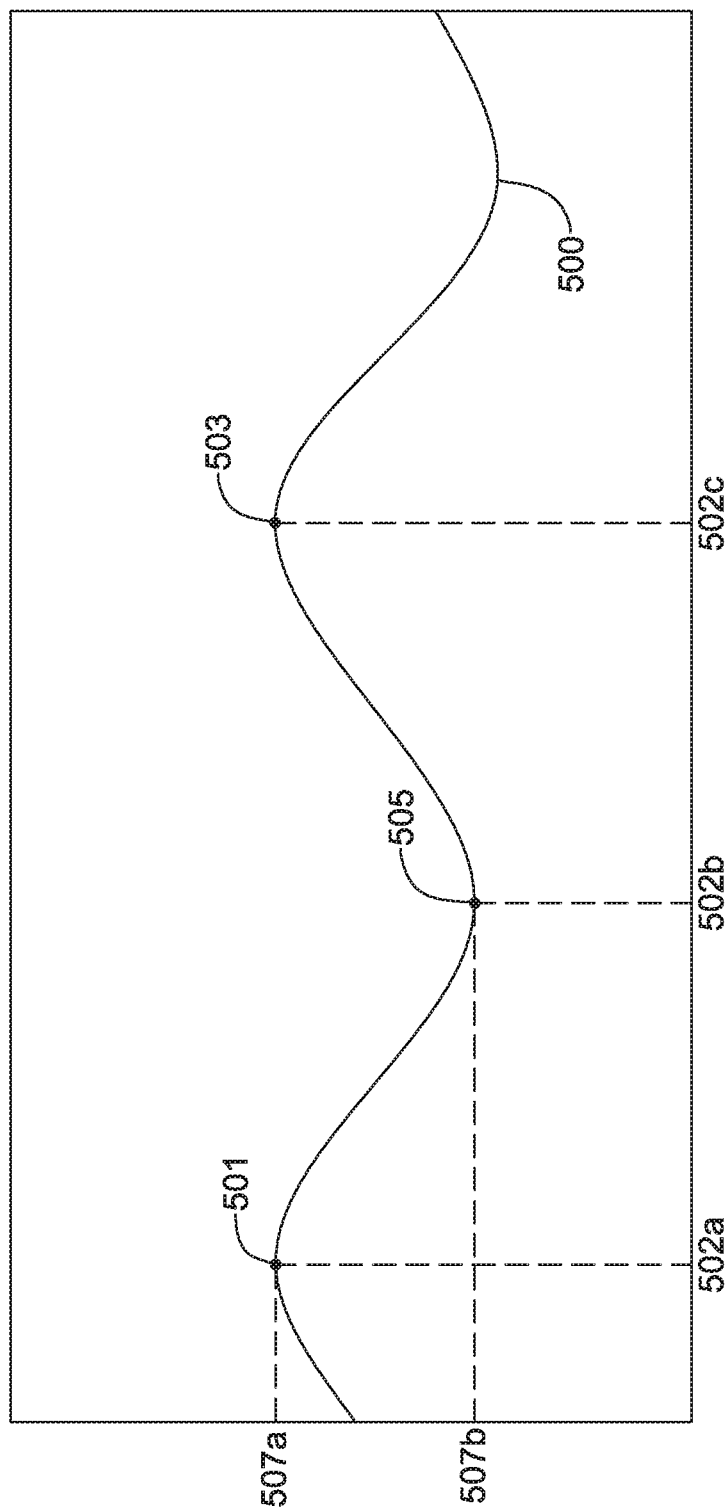
FIG. 5 is a graph of a low-pass filtered signal generated by low pass-filtering the integrated signal of FIG. 4.

In some alternative or additional embodiments, LCP 100 may process integrated signal 400 before determining a respiration rate. For instance, LCP 100 may pass integrated signal 400 through a low pass filter. An illustrative filtered signal 500, shown in FIG. 5, represents an output after low-pass filtering integrated signal 400. The peaks and valleys, for examples peaks 501 and 503 and valley 505, of filtered signal 500 may represent the inhalations and exhalations of the patient, respectively. In on example, LCP 100 may determine timings of the inflections of filtered signal 500 by taking the first derivative of filtered signal 500 and finding the zero-crossings. Then, the differences in timings between two peaks (or two valleys) may be used to determine a respiration rate. For examples, LCP 100 may take the difference in timing between time 502a and time 502c, and divide sixty by the resulting difference to determine a respiration rate in breaths per minute.

Alternative embodiments may process raw accelerometer data 200 in a different manner than described with respect to FIGS. 2-5. For instance, LCP 100 may apply a low pass filter directly to raw accelerometer data 200. LCP 100 may use a filter that has a corner frequency of, for example, between 0.3 Hz and 0.7 Hz, and in some examples, LCP 100 may use a filter with a corner frequency of 0.5 Hz. In such embodiments, the resulting filtered signal may look similar to filtered signal 500. In these instances, and as one example, LCP 100 may find zero-crossing of the first derivative of the filtered signal to find inflection points, and may use the timings of those inflection points to determine a respiration rate.

In alternative embodiments, instead of determining a respiration rate, LCP 100 may adjust the rate of delivery of the electrical stimulation pulses based on a frequency of a signal, such as filtered signal 500. For instance, as the patient's respiration rate increases, the relative power of the frequency components of filtered signal 500 may skew towards higher frequencies. Accordingly, after determining changes in the relative power of the frequency components of filtered signal 500, LCP 100 may adjust the rate of delivery of the electrical stimulation pulses based on those determined changes. In some cases, this may be less computationally intensive, and/or may yield more accurate data about the current respiration of the patient.

In still other additional or alternative embodiments, LCP 100 may sample the accelerometer signal at a fixed rate, for instance at a fixed point in the cardiac cycle. In some examples, LCP 100 may sample the accelerometer signal at times corresponding to sensed R-waves. For instance, LCP 100 may use a peak detector, or one or more other techniques, to determine occurrences of R-waves in sensed cardiac electrical signals. LCP 100 may then sample the accelerometer signal when LCP 100 determines an occurrence of an R-wave. Although, in other embodiments, LCP 100 may sample the accelerometer signal at other fixed points in the cardiac cycle. This sampled accelerometer signal may be used by LCP 100 in a similar manner to that described with respect to filtered signal 500, for example in determining respiration rates and/or relative tidal volumes, as described herein.

It should be understood that although the above description revolved around determining a respiration rate based on accelerometer data, other signals can be used to determine a respiration rate. For instance, LCP 100 may use ECG data to determine a respiration rate. When LCP 100 is implanted within a chamber of the heart, LCP 100 may sense intracardiac electrical signals, for example represented by an ECG, via a sense amplifier or the like. The relative magnitude of the R-wave of the ECG signal may fluctuate with changes in the volume of the heart chamber, and the volume of the heart chamber may fluctuate as a function of intrathoracic pressure—such as due to changes in lung volume of the patient. In some instances, such changes in intracardiac pressure may be used to determine respiration rate.

In some instances, LCP 100 may use a parameter other than respiration rate to adjust the rate of delivery of the electrical stimulation pulses. For instance, LCP 100 may use heart sounds to adjust the rate of delivery of the electrical stimulation pulses. Increased heart sounds, and specifically increased S1 heart sounds, may be an indication of increased contractility of the heart. Examples of increased heart sounds may include an increase in the amplitude of the heart sounds signal, or an increase in the duration of the signal peaks. Increased contractility of the heart may indicate a need for increased cardiac output. Accordingly, as the heart sounds increase, LCP 100 may increase the rate of delivery of the electrical stimulation pulses, for example in a manner similar to that described with respect to respiration rate. In some cases, LCP 100 may use temperature to adjust the rate of delivery of the electrical stimulation pulses. For instance, increased blood temperature may indicate increased metabolic activity of the body, and accordingly, a need for increased cardiac output.

In some instances, LCP 100 may use a relative tidal volume parameter to adjust the rate of delivery of the electrical stimulation pulses. For example, LCP 100 may determine a relative tidal volume parameter from integrated signal 400, or in other examples, filtered signal 500. As can be seen in FIG. 4, where LCP 100 determines a relative tidal volume parameter, LCP 100 may determine peaks 401 that are local minimums, for example, peak 401f. LCP 100 may determine peaks 401 that are local minimums in a similar manner to how LCP 100 may determine peaks 401 that are local maximums. For instance, LCP 100 may identify peaks whose value is lower than the immediately preceding and following peaks. LCP 100 may then determine a difference in values between peak 401f, having value 407b, and the preceding local maximum peak, such as peak 401b in FIG. 4, having value 407a. LCP 100 may use this difference in values between values 407a and 407b to provide a measure related to the relative tidal volume parameter. Increases in the relative tidal volume, or increases in the variability of the relative tidal volume, may indicate an increased need for cardiac output. Accordingly, LCP 100 may track how the relative tidal volume changes over time and may adjust the rate of delivery of the electrical stimulation pulses based on the changes in relative tidal volume, for instance possibly in a similar manner to respiration rate. Where LCP 100 further low-pass filters integrated signal 400, or directly low-pass filters raw accelerometer data 200 to produce filtered signal 500, LCP 100 may determine a relative tidal volume parameter from filtered signal 500. For instance, LCP 100 may determine a difference in values 507a and 507b between peak 501 and valley 505. LCP 100 may use this determined difference as a measure related to the relative tidal volume parameter value.

Figure 6:
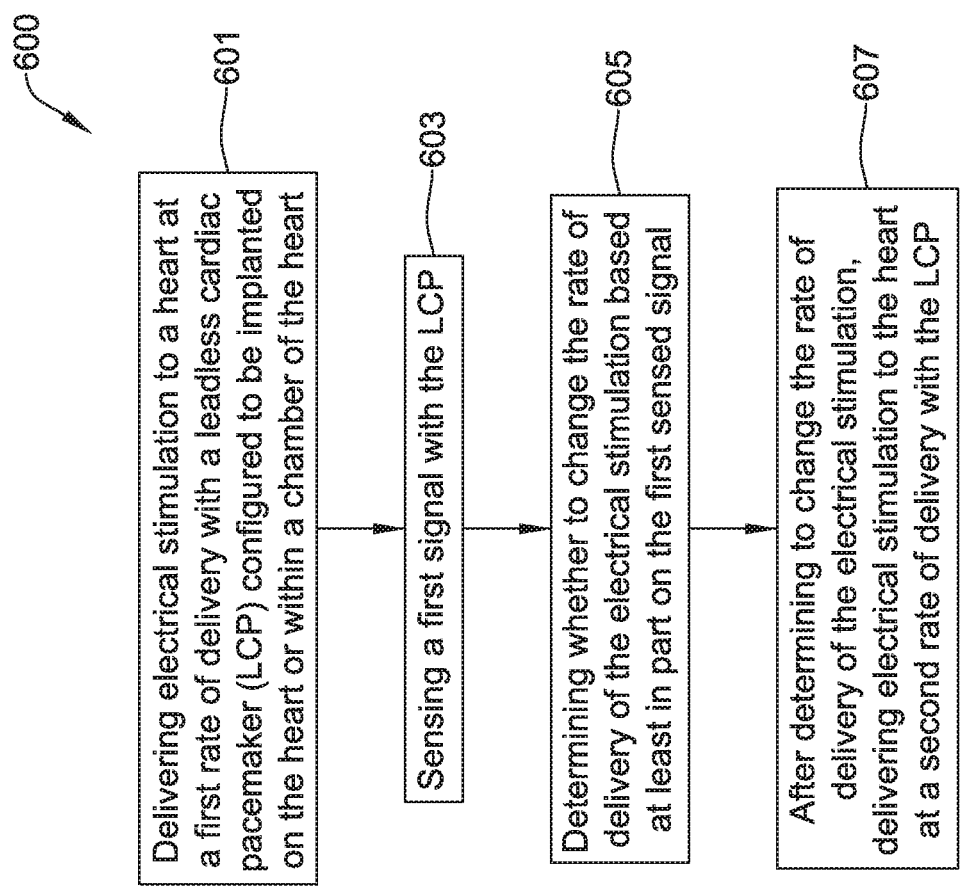
FIG. 6 is a flow diagram of an illustrative method that may be implemented by a medical device or medical device system, such as the illustrative LCP of FIG. 1.

FIG. 6 depicts a general method 600 for how a device, such as LCP 100, may adjust the rate of delivery of the electrical stimulation pulses. Illustrative method 600 begins with delivering electrical stimulation to a heart at a first rate of delivery with a leadless cardiac pacemaker (LCP) configured to be implanted on the heart or within a chamber of the heart, as indicated at 601. The LCP may be an LCP such as LCP 100 described with respect to FIG. 100. Next, method 600 may sense a first signal with the LCP, as at 603. As described above, the signal may be a signal such as an accelerometer signal, an ECG, a heart sounds signal, a pressure signal, or a temperature signal or the like. Next, method 600 may determine whether to change the rate of delivery of the electrical stimulation based at least in part on the first sensed signal, as at 605. As mentioned, in some instances, the LCP may determine a parameter based on the first sensed signal, such as a respiration rate, and may adjust the rate of delivery of the electrical stimulation pulses based on the determined parameter. In some cases, the LCP may determine a relative tidal volume parameter, a heart sounds parameter, and/or an intracardiac pressure parameter. Where the LCP determines a parameter based on the first sensed signal, the LCP may further determine whether to change the rate of electrical stimulation based at least in part on the determined parameter instead of or in addition to the first sensed signal. For instance, the LCP may determine to change the rate of delivery of electrical stimulation in response to the determined parameter rising above or falling below, as appropriate, a threshold. As one illustrative example, the LCP may determine to increase the rate of delivery of electrical stimulation in response to determining the respiration rate parameter rises above a threshold, thereby indicating an increased need for cardiac output. After determining to change the rate of delivery of the electrical stimulation, method 600 may continue with delivering electrical stimulation to the heart at a second rate of delivery with the LCP, as at 607. For instance, if the first sensed signal, or determined parameter, indicates a need for increased cardiac output, the LCP may increase the rate of delivery of the electrical stimulation. Conversely, if the first sensed signal, or determined parameter, does not indicate a need for the current cardiac output, the LCP may decrease the rate of delivery of the electrical stimulation.

In some cases, LCP 100 may adjust the rate of delivery of the electrical stimulation based on a combination of sensed signals. For instance, LCP 100 may sense a first signal and, based on the sensed first signal, determine a respiration rate. LCP 100 may further determine a second parameter in addition to respiration rate. In some examples, LCP 100 may determine the second parameter also from the acceleration signal, for instance a relative tidal volume parameter. In other examples, LCP 100 may sense a second signal, for instance a heart sounds signal, an intracardiac pressure signal, a temperature signal, and/or the like, and may determine a second parameter from the sensed second signal. LCP 100 may determine a heart sounds parameter, an intracardiac pressure parameter, and/or a temperature parameter. In some alternative examples, LCP 100 may determine a second respiration rate based on the sensed second signal.

After determining the second parameter, LCP 100 may use a combination of the determined respiration rate and the determined second parameter to adjust the rate of delivery of the electrical stimulation. For instance, LCP 100 may follow a method according to FIG. 7. FIG. 7 depicts a flow diagram of method 700 that LCP 100 may follow in order to adjust the rate of delivery of the electrical stimulation pulses. Method 700 begins with LCP 100 determining if a first one of the determined respiration rate or a second determined parameter indicates a need for increased cardiac output, as at 701. For example, and in some cases, the determined respiration rate or the determined second parameter may rise above a corresponding threshold, or may fall below a corresponding threshold where appropriate. The determined respiration rate or the second determined parameter rising above a threshold or falling below a threshold may indicate a need for increased cardiac output. If neither of the respiration rate nor the second determined parameter indicates a need for increased cardiac output, LCP 100 may follow the NO branch of step 701, maintain the current rate of delivery of the electrical stimulation pulses as shown at 707, and continue to monitor the respiration rate and the determined second parameter until one of the parameters does indicate a need for increased cardiac output at 701.

Where LCP 100 determines that the determine respiration rate or the determined second parameter do indicate a need for increased cardiac output, LCP 100 may follow the YES branch of step 701. LCP 100 may then determine whether the second one of the determined respiration rate and the second determined parameter indicate a need for increased cardiac output, as at 703. If LCP 100 determines that the second one of the determined respiration rate and the second determined parameter does not indicate a need for increased cardiac output, LCP 100 may follow the NO branch of step 703, maintain the current rate of delivery of the electrical stimulation pulses as shown at 707, and continue to monitor the respiration rate and the determined second parameter until one of the parameters does indicate a need for increased cardiac output at 701. However, if LCP 100 determines that the second one of the determined respiration rate and the second determined parameter indicates a need for increased cardiac output, i.e. both the determined respiration rate and the second determined parameter indicate a need for increased cardiac output, LCP 100 may adjust the rate of delivery of electrical stimulation pulses, as at 705. For instance, LCP 100 may increase the rate of delivery of the electrical stimulation pulses.

While the example method of FIG. 7 references a determined respiration rate and a second determined parameter, it is contemplated that any two (or more) parameters may be used. For example, a heart sounds parameter and a relative tidal volume parameter may be used. In some case, the rate of delivery of electrical stimulation pulses may not be adjusted unless three or more parameters indicates a need for increased cardiac output, or two out of three parameters indicates a need for increased cardiac output. These are just some examples.

In some cases, LCP 100 may determine and monitor two parameters, such as respiration rate and the second determined parameter as above, but still adjust the rate of delivery of the electrical stimulation pulses based on only the determined respiration rate. In some cases, if LCP 100 determines that both the determined respiration rate and the second determined parameter indicate a need for increased cardiac output, LCP 100 may adjust the rate of delivery of the electrical stimulation pulses even further. For instance, if one of the determined respiration rate and the second determined parameter indicate a need for increased cardiac output, LCP 100 may increase the rate of delivery of the electrical stimulation pulses. If LCP 100 determines that both the determined respiration rate and the second determined parameter indicates a need for increased cardiac output, LCP 100 may increase the rate of delivery of the electrical stimulation pulses even further. In some cases, LCP 100 may have two gain factors stored in memory and may apply the first gain factor to adjusting the rate of delivery of the electrical stimulation pulses after determining that only one of the determined respiration rate and the second determined parameter indicate a need for increased cardiac output. The LCP 100 may apply the second gain factor to adjusting the rate of delivery of the electrical stimulation pulses after determining that both the determined respiration rate and the second determined parameter indicate a need for increased cardiac output, where the second gain factor is greater than the first gain factor. Of course, in such examples, LCP 100 may still further adjust the rate of delivery of the electrical stimulation pulses if LCP 100 determines further changes to the first one of the determined respiration rate and/or the second determined parameter.

In yet another example, LCP 100 may use multiple parameters in sequence to determine whether to adjust the rate of delivery of the electrical stimulation pulses. For instance, LCP 100 may first determine whether a respiration rate parameter changes. Once LCP 100 has determined that the respiration rate parameter has changed, for example increased above a threshold, LCP 100 may then increase the rate of delivery of the electrical stimulation pulses to a first increased rate. Once LCP 100 is delivering the electrical stimulation pulses at the first increased rate, LCP 100 may monitor a second parameter for changes to further adjust the rate of delivery of the electrical stimulation pulses. For instance, LCP 100 may monitor the relative tidal volume for changes in determining whether to further adjust the rate of delivery of the electrical stimulation pulses. If LCP 100 determines changes in the relative tidal volume parameter, for example increases in the relative tidal volume parameter above a threshold, LCP 100 may further increase the rate of delivery of the electrical stimulation pulses to a second increased rate. Of course, in other examples, the order of the sequence of the monitored parameters may be different. Generally, this disclosure contemplates embodiments including any number and any combination of parameters arranged in any order.

Although the above methods for adjusting the rate were described with respect to increasing the rate of delivery of the electrical stimulation pulses when one or more parameters indicate a need for increased cardiac output, in a similar manner LCP 100 may decrease the rate of delivery of the electrical stimulation pulses when the one or more parameters do not indicate a need for the current level of cardiac output. For instance, when one or more of the parameters fall below a threshold, or rise above a threshold where appropriate, which indicates less need that is provided by the current cardiac output, and hence the current rate of delivery of the electrical stimulation pulses. Accordingly, LCP 100 may be configured to decrease the rate of delivery of the electrical stimulation pulses to reduce the cardiac output. In some embodiments, LCP 100 may use multiple determined parameters to aid in determining whether to decease the rate of delivery of the electrical stimulation pulses, for example in a similar manner described with respect to FIG. 6 for increasing the rate of delivery of the electrical stimulation pulses.

Additionally, although the above methods for adjusting the rate of delivery of the electrical stimulation pulses were described with respect to respiration rate and another parameter, in alternative embodiments, LCP 100 may use two parameters that do not include respiration rate to determine whether to adjust the rate of delivery of the electrical stimulation pulses. For instance, LCP 100 may use a heart sounds parameter and a relative tidal volume parameter. In other instance, LCP 100 may use an intracardiac pressure parameter and a temperature parameter. In general, LCP 100 may use any combination of parameters described herein in determining whether to adjust the rate of delivery of the electrical stimulation pulses. In still some examples, both parameters may be respiration rate parameters. However, both respiration rate parameters may be determined using different signal sources or using different signal processing algorithms. For example, LCP 100 may determine a first respiration rate parameter based on an accelerometer signal and a second respiration rate parameter based on an ECG signal, or an intracardiac signal, or another sensed signal as desired. In such examples, the LCP 100 may consider two respiration rates based on two different signals when adjusting the rate of delivery of the electrical stimulation pulses.

Although not explicitly mentioned previously, where LCP 100 includes an accelerometer, the accelerometer may be a three-axis accelerometer. Where LCP 100 includes a three-axis accelerometer, raw accelerometer data 200 may be a summation from all three channels of the three-axis accelerometer, a summation from two of the three channels, or may be only one of the three channels. LCP 100 may then proceed to process raw accelerometer data 200 as described herein. In some cases, LCP 100 may be configured to low-pass filter each channel of the three-axis accelerometer separately. LCP 100 may then use the resulting filtered signal of the three filtered signals that most closely correlates with a template signal. In some instances, the template signal may be similar to filtered signal 500. In still other examples, a user may view each of the three filtered signals and program LCP 100 to use a specific one of the filtered signals.

Aside from differences in how LCP 100 may operate with respect to how LCP 100 processes the accelerometer data where LCP 100 includes a three-axis accelerometer, in some embodiments, LCP 100 may change one or more ways in which LCP 100 determines parameters or one or more of the steps LCP 100 uses to adjust the rate of delivery of the electrical stimulation pulses. For instance, based on the three-axis accelerometer signals, LCP 100 may be able to determine whether the patient has a supine or erect posture. Based on the determination, LCP 100 may enable or disable rate-adaptive pacing. For instance, if the patient is in a supine position, LCP 100 may disable rate-adaptive pacing. In other instances, LCP 100 may change the specific method by which LCP 100 adjusts the rate of delivery of the electrical stimulation pulses, or even the gain factor used in determining by how much to adjust the rate of delivery of the electrical stimulation pulses, based on whether the patient is in a supine or erect position.

It is contemplated that LCP 100 may include one or more pre-programmed parameters. For instance, LCP 100 may include pre-programmed respiration rate thresholds, or thresholds associated with other parameters. Additionally, the various thresholds may be associated with one or more rates of delivery of the electrical stimulation pulses. In examples where LCP 100 may adjust the rate of delivery of the electrical stimulation pulses based on one or more gain factors, LCP 100 may be pre-programmed with the one or more gain factors. In some instances, some or all of these pre-programmed values may be programmable and changeable. For instance, LCP 100 may be able to communicate with a programming device located external to the patient. A user of the programming device, such as a physician, may enter changes to the one or more programmable values into the programming device. The programming device may then communicate the changed values to LCP 100 where the changed values overwrite the previous pre-programmed values. In addition, in some examples, LCP 100 may be pre-programmed with multiple methods for determining whether to adjust the rate of delivery of the electrical stimulation pulses. LCP 100 may operate according to one of the methods at a time, whichever method is the active method. In some examples, the programming device may be able to communicate with the LCP 100 to change the active method, or even to communicate a new method for storage into a memory of LCP 100.

In some instances, LCP 100 may be calibrated from time to time. For example, LCP 100 may be calibrated following implantation in a patient, or during subsequent follow-up clinic visits. To calibrate LCP 100, a patient may be hooked up to an external respiration sensor, such as a spirometer, or a respiratory inductance plethysmography machine, or the like. Signals collected from these respiration instruments may be compared to the determined respiration rate of LCP 100. Where there are differences between the respiration rate determined by LCP 100 and the output of the respiration instrument or instruments, a user, such as a physician, may calibrate the specific algorithm used by LCP 100 to determine the respiration rate. For instance, the user may alter the specific algorithm by which LCP 100 determines the respiration rate—for example the user may switch LCP 100 from using one of the methods described herein to another one of the methods described herein. Alternatively, the user may alter specific parameters of the current method by which LCP 100 is operating. For instance, where LCP 100 employs one or more filters, the user may adjust the corner frequencies of the filters. Alternatively, where LCP 100 includes multiple electrodes, the user may adjust the specific electrodes via which LCP 100 senses cardiac electrical signals. In still other embodiments, the user may alter other aspect of LCP 100 or the particular method by which LCP 100 determines a respiration rate.

In some examples where LCP 100 is calibrated, a user may employ a two-point calibration process. For instance, a user may calibrate LCP 100 while the patient is in a resting state. The user may then further calibrate LCP 100 while the patient is undergoing physical exertion, such as while the patient is walking or running, or climbing stairs, or the like.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A method of delivering electrical stimulation to a heart of a patient, the method comprising:
   sensing a first signal with a leadless cardiac pacemaker (LCP) configured to be implanted on the heart or within a chamber of the heart, wherein the first signal is an accelerometer signal;
   determining an absolute value of the first sensed signal;
   determining an integrated signal over each of a plurality of time periods occurring during each of a plurality of respiration cycles of the patient using the absolute value of the first sensed signal;
   determining a respiration rate based at least in part on the determined integrated signals; and
   setting a rate of delivery of electrical stimulation based at least in part on the determined respiration rate.

2. The method of claim 1, wherein determining a respiration rate based on the integrated signals comprises determining a difference in timing between a pair of peaks of the integrated signals.

3. The method of claim 2, wherein the value of each peak of the pair of peaks are local maximums.

4. The method of claim 1, wherein determining a respiration rate based on the integrated signals further comprises:
   low-pass filtering the integrated signal;
   determining zero-crossings of the first derivative of the low-pass filtered signal; and
   determining a difference in timing between a pair of zero-crossings of the first derivative of the low-pass filtered signal.

5. The method of claim 1, further comprising:
   identifying cardiac cycles of the patient; and
   each of the plurality of time periods correspond to a cardiac cycle of the patient.

6. A medical device for delivering electrical stimulation to a heart of a patient, the medical device comprising:
- a housing configured to be implanted on the heart or within a chamber of the heart;
- one or more electrodes connected to the housing; and
- a controller disposed within the housing, the controller configured to:
  - sense a first signal that is an accelerometer signal;
  - determine an absolute value of the first sensed signal;
  - determine an integrated signal over each of a plurality of time periods occurring during each of a plurality of respiration cycles of the patient using the absolute value of the first sensed signal;
  - determine a respiration rate based on the integrated signal; and
  - set a rate of delivery of electrical stimulation by the medical device based at least in part on the determined respiration rate.

7. The medical device of claim 6, wherein the controller is configured to determine the respiration rate based at least in part on a difference in timing between a pair of peaks of the integrated signals.

8. The medical device of claim 7, wherein each peak of the pair of peaks are local maximums.

9. The medical device of claim 6, wherein determining the respiration rate comprises:
- low-pass filtering the integrated signal;
- determining zero-crossings of a first derivative of the low-pass filtered signal; and
- determining a difference in timing between a pair of zero-crossings of the first derivative of the low-pass filtered signal.

10. The medical device of claim 6, wherein the controller is configured to:
- identifying cardiac cycles of the patient; and
- each of the plurality of time periods correspond to a cardiac cycle of the patient.

11. A leadless cardiac pacemaker for delivering electrical stimulation to a heart of a patient, the medical device comprising:
- a housing configured to be implanted within a chamber of the heart;
- one or more electrodes connected to the housing; and
- a controller disposed within the housing, the controller configured to:
  - sense a first signal that is an accelerometer signal;
  - determining an absolute value of the first signal;
  - determine an integrated signal over each of a plurality of time periods occurring during each of a plurality of respiration cycles of the patient using the absolute value of the first signal;
  - determine a respiration rate based at least in part on the determined integrated signals; and
  - set a rate of delivery of electrical stimulation to the heart by the leadless cardiac pacemaker based at least in part on the determined respiration rate.

12. The leadless cardiac pacemaker of claim 11, wherein the controller is configured to determine the respiration rate based at least in part on a difference in timing between a pair of peaks of the integrated signals.

13. The leadless cardiac pacemaker of claim 12, wherein each peak of the pair of peaks are local maximums.

14. The leadless cardiac pacemaker of claim 11, wherein the controller is configured to:
- identifying cardiac cycles of the patient; and
- each of the plurality of time periods correspond to a cardiac cycle of the patient.

\* \* \* \* \*